United States Patent
Lee et al.

(10) Patent No.: US 6,337,346 B1
(45) Date of Patent: Jan. 8, 2002

(54) NAPHTHO- AND DIHYDROBENZO-THIOPHENE DERIVATIVES AS CYTOTOXIC ANTITUMOR AGENTS

(75) Inventors: Kuo-Hsiung Lee, Chapel Hill, NC (US); Sheng-Chu Kuo, Tai Chung (TW)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/651,357

(22) Filed: Aug. 30, 2000

Related U.S. Application Data

(63) Continuation of application No. 09/092,929, filed on Jun. 5, 1998, now Pat. No. 6,174,913.

(51) Int. Cl.$^7$ .................. A61K 31/38; C07D 333/74
(52) U.S. Cl. ............... 514/443; 549/43; 549/44; 549/45; 549/48
(58) Field of Search ............... 549/43, 44, 45, 549/48; 514/443

(56) References Cited

U.S. PATENT DOCUMENTS

| | | | |
|---|---|---|---|
| 4,183,943 A | 1/1980 | Bastian | 424/275 |
| 4,185,110 A | 1/1980 | Eichenberger et al. | 424/275 |
| 4,419,354 A | 12/1983 | Child et al. | 424/248.56 |
| 4,740,518 A | 4/1988 | Bollinger | 514/443 |
| 4,866,070 A | 9/1989 | Bair | 514/280 |
| 4,952,602 A | 8/1990 | Iwasaki et al. | 514/443 |
| 4,965,285 A | 10/1990 | Bair | 514/443 |
| 5,017,600 A | 5/1991 | Bair | 514/443 |
| 5,151,528 A * | 9/1992 | Mukai et al. | 549/31 |
| 5,292,894 A | 3/1994 | Ebel et al. | 549/43 |
| 5,530,139 A | 6/1996 | Saida et al. | 549/3 |
| 5,645,988 A * | 7/1997 | Vande Woude et al. | |
| 5,679,694 A | 10/1997 | Franzmann et al. | 514/339 |
| 5,718,997 A * | 2/1998 | Hayata et al. | |
| 5,728,846 A | 3/1998 | Vuligonda et al. | 549/16 |
| 5,856,341 A | 1/1999 | Bell et al. | 514/324 |

FOREIGN PATENT DOCUMENTS

| | | |
|---|---|---|
| DE | 2803984 A1 | 8/1978 |
| DE | 2804777 A1 | 8/1978 |
| EP | 0183439 A2 | 6/1986 |
| EP | 0221345 A1 | 5/1987 |
| EP | 0466094 A2 | 1/1992 |
| GB | 2011455 | 7/1979 |
| JP | 59027894 A | 2/1984 |

OTHER PUBLICATIONS

Fichentscher et al.: Color reactions of 2, 3–dicyano–1–4–dithiaanthraquinone, *Arch. Pharm.* 301:8 588–592 (1968) (XP–000856359).

Farina et al.: "Reaction of 2–acetyl–1, 4–benzoquinone and quinone analogs with thiols. Application to the synthesis of thiophenequinones", *An. Quim.* 72:11–12 902–909 (1976) (XP–000856444).

Yamashita et al.: "Novel Quinon–type Acceptors fused with Sulfur Heterocycles and their Highly Conductive Complexes with Electron Donors", *J. Chem. Soc., Chem. Commun.* 1489–1491 (1986) (XP–002123041).

Acosta et al.: "Microwave Assisted Synthesis of Heterocyclic Fused Quinones in Dry Media", *Tetrahedron Letters* 36:12 2165–2168 (1995) (XP004028432).

Zani et al., "Anti–Plasmodial and Anti–Trypanosomal Activity of Synthetic Naphtho [2,3–b] thiophen–4,9–quinones", *Bioorganic & Medicinal Chemistry* 5:12 2185–2192 (1997) (XP–000856330).

Tonholo et al.; "Electrochemical Properties of Biologically Active Heterocyclic Naphthoquinones", *Journal of Braz. Chem. Soc.* 9:2 163–169 (1998) (XP–000856331).

(List continued on next page.)

*Primary Examiner*—Deborah C. Lambkin
(74) *Attorney, Agent, or Firm*—Myers Bigel Sibley & Sajovec

(57) ABSTRACT

Compounds useful as cytotoxic agents are selected from the group consisting of compounds of Formula I and compounds of Formula II:

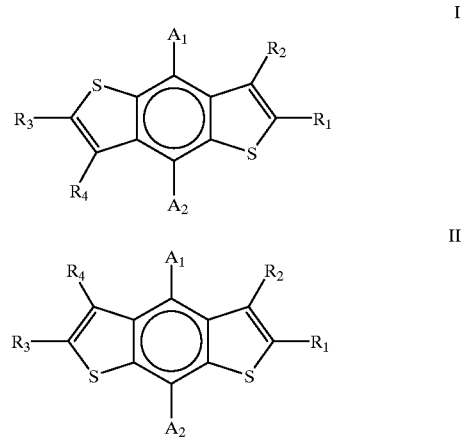

wherein: $R_1$, $R_2$, $R_3$ and $R_4$ are each independently selected from the group consisting of: hydrogen, alkyl, carboxy, alkoxy, hydroxyalkyl, alkylcarbonyl; alkylcarbonyloxy; alkyl substituted with alkylcarbonyloxy, thiophenylcarbonyl; nitro and cyano; thiophenyl and thiophenylthiophenyl, each of which may be unsubstituted or substituted with alkyl, carboxy, alkoxy, hydroxyalkyl, alkylcarbonyl; alkylcarbonyloxy; alkyl substituted with alkylcarbonyloxy, nitro or cyano; subject to the proviso that at least one of $R_1$, $R_2$, $R_3$ and $R_4$ is not hydrogen; $A_1$ and $A_2$ are each selected from the group consisting of: =O, alkyl, alkoxy, and alkylcarbonyloxy; and the pharmaceutically acceptable salts thereof. When $A_1$ and $A_2$ are =O, the center ring has only two, and not three, double bonds.

7 Claims, No Drawings

OTHER PUBLICATIONS

Huang et al.: "Synthesis and Cytotoxicity of Acetyl–4H, 9H–Naphtho [2,3–b] Thiophene–4,9–Diones", *Bioorganic & Medical Chemistry Letters* 8 2763–2768 (1998) (XP004139616).

Database WPI Week 199920, abstract *Derwent Publications Ltd.*, London, GB; AN 1999–236677 & JP 11 065141 A (1999) (XP–002123046).

Database WPI Week 199925, abstract *Derwent Publications Ltd.*, London, GB; AN 1999–292192 & JP 11 095465 A (1999) (XP–002123047).

Meth–Cohn et al.; "CA75:20374", 1971.
Katritzky et al.; "CA 127:176313", 1997.
Trincone et al.; "CA 105:130410", 1986.
Tonholo et al.; "CA 129:128195", 1998.
Carey et al, Chem. Abs. No. 92:148514, 1980.*
Hayata et al, Chem. Abs. No. 123:156389, 1995.*
Kikuchi et al, Chem. Abs. No. 116:245248, 1992.*
Yamashita et al, Chem. Abs. No. 107:6620, 1987.*
Vande Woude et al, Chem. Abs. 127:130982, 1997.*

* cited by examiner

NAPHTHO- AND DIHYDROBENZO-THIOPHENE DERIVATIVES AS CYTOTOXIC ANTITUMOR AGENTS

This application is a continuation of Ser. No. 09/092,929 filed on Jun. 5, 1998, now U.S. Pat. No. 6,174,913.

This invention was made with Government support under grant number CA-17627 from the National Institutes of Health. The Government has certain rights to this invention.

FIELD OF THE INVENTION

The present invention concerns naphtho and dihydrobenzo-thiophene derivatives, which are active as antitumor agents and in inhibiting cellular mitosis, along with pharmaceutical formulations containing the same.

BACKGROUND OF THE INVENTION

Many naturally occurring substituted anthraquinone and naphthoquinones possess cytotoxic antileukemic activities (Zee-Cheng P. et al., *J. Med. Chem.* 1979, 22, 501–505; Chang, P., Lee, K. H. *Phytochemistry.* 1984, 23, 1733–1736; T. Hayashi, F. Smith, and K. H. Lee, K. H. *J. Med. Chem.* 1987, 30, 2005–2008). In addition, the natural furanonaphthoquinones 1 and 2 and their synthetic analog 3 (see figures below) show potent cytotoxicity against KB cells with $ED_{50}$ values of 1.0, 2.0, and 0.3 µg/mL, respectively (Rao, M. M.; Kingston, D. G. I. *J. Nat. Prod.* 1982, 45, 600–604).

The unsubstituted thiophene derivative naphtho[2,3-b]thiophene-4,9-dione (4) also was found to be cytotoxic against KB cells with an $ED_{50}$ value of 1.4 µg/mL (Goncalves, R.; Brown, E. V. *J. Org. Chem.* 1952, 17, 698–704; Weinmayr, V. U.S. Pat. No. 2,497,334 1950; Weinmayr, V. *J. Am. Chem. Soc.* 1952, 74, 4353–4357; Carruthers, W.; Douglas, A. G.; Hill, J. *J. Chem. Soc.* 1962, 704–708; Carruthers, W. *J. Chem. Soc.* 1963, 4477–4483; Tagawa, H.; Ueno, K. *Chem. Pharm. Bull.* 1978, 26, 1384–1393; Huang, L. J.; Kuo, S. C.; Perng, C. Y.; Chao, Y. H.; Wu, T. S.; McPhail, A. T.; Cheng, H. H.; Lee, K. H. Bioorg & Med. Chem. Letters, submitted.) Introduction of a lipophilic acetyl group gave 2-acetyl naphtho[2,3-b]thiophene-4,9-dione (5) with enhanced cytotoxicity ($ED_{50}$= 0.4 µg/mL)(Huang, L. J.; Kuo, S. C.; Perng, C. Y.; Chao, Y. H.; Wu, T. S.; McPhail, A. T.; Cheng, H. H.; Lee, K. H. Bioorg & Med. Chem. Letters, submitted).

SUMMARY OF THE INVENTION

A first aspect of the present invention is a compound selected from the group consisting of compounds of Formula I and compounds of Formula II:

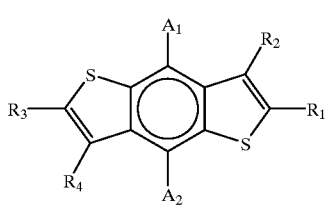

I

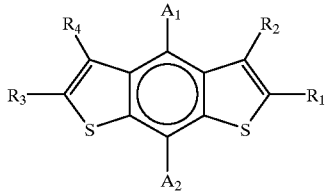

II wherein:

$R_1$, $R_2$, $R_3$ and $R_4$ are each independently selected from the group consisting of:
hydrogen, alkyl, carboxy, alkoxy, hydroxyalkyl, alkylcarbonyl; alkylcarbonyloxy; alkyl substituted with alkylcarbonyloxy, thiophenylcarbonyl; nitro and cyano;
thiophenyl and thiophenylthiophenyl, each of which may be unsubstituted or substituted with alkyl, carboxy, alkoxy, hydroxyalkyl, alkylcarbonyl; alkylcarbonyloxy; alkyl substituted with alkylcarbonyloxy, nitro or cyano;
subject to the proviso that at least one of $R_1$, $R_2$, $R_3$ and $R_4$ is not hydrogen;
$A_1$ and $A_2$ are each selected from the group consisting of: =O, alkyl, alkoxy, and alkylcarbonyloxy;
and the pharmaceutically acceptable salts thereof.

Note that, When $A_1$ and $A_2$ are =O, the center ring has only two, and not three, double bonds, as shown in Formula Ia and IIa below.

In a preferred embodiment of the foregoing, at two or (most preferably) three of $R_1$, $R_2$, $R_3$ and $R_4$ are hydrogen.

A second aspect of the present invention is a compound according to Formula III:

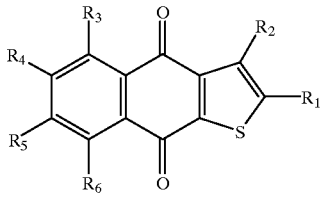

III wherein:

$R_1$, $R_2$, $R_3$, $R_4$, $R_5$ and $R_6$ are each independently selected from the group consisting of:
hydrogen, alkyl, carboxy, alkoxy, hydroxyalkyl, alkylcarbonyl, alkylcarbonyloxy, alkyl substituted with alkylcarbonyloxy, thiophenylcarbonyl; nitro and cyano;
thiophenyl and thiophenylthiophenyl, each of which may be unsubstituted or substituted with alkyl, carboxy, alkoxy, hydroxyalkyl, alkylcarbonyl, alkylcarbonyloxy, alkyl substituted with alkylcarbonyloxy, nitro or cyano;
subject to the proviso that at least one of $R_1$, $R_2$, $R_3$ and $R_4$ is not hydrogen;
and the pharmaceutically acceptable salts thereof.

A further aspect of the present invention is a composition comprising an effective antitumor amount of a compound of Formula I, II or III above, or a pharmaceutically acceptable salt thereof, in a pharmaceutically acceptable carrier.

A further aspect of the present invention is a method for treating a tumor, the method comprising administering to a subject in need of treatment a compound of Formula I, II or III above, or a pharmaceutically acceptable salt thereof, in an amount effective to treat said tumor.

A still further aspect of the present invention is a method for inhibiting cellular mitosis, said method comprising contacting a cell with a compound of Formula I, II or III above, or a pharmaceutically acceptable salt thereof, in an amount effective to inhibit cellular mitosis.

A still further aspect of the present invention is the use of a compound of Formula I, II or III above, or a pharmaceutically acceptable salt thereof, for the preparation of a medicament for carrying out the methods described above.

DETAILED DESCRIPTION OF THE INVENTION

The term "alkyl" as used herein, inidividually or as a portion of another substituent term such as "alkoxy", refers to C1 to C4 alkyl, which may be linear or branched, and saturated or unsaturated. Preferably, the alkyl is saturated, and preferably the alkyl is linear.

The term "halogen" or "halo" as used herein refers to fluorine, chlorine, bromine, iodine, etc., or fluoro, chloro, bromo, iodo, etc., respectively.

Compounds of the present invention can be made in accordance with known techniques, or variations thereof which will be apparent to those skilled in the art in given the Examples set forth below.

Specific examples of compounds of Formula I and II are compounds of Formula Ia and compounds of Formula IIa:

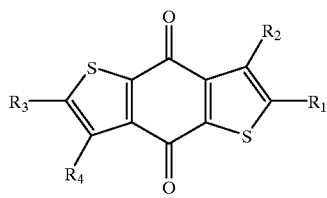

Ia

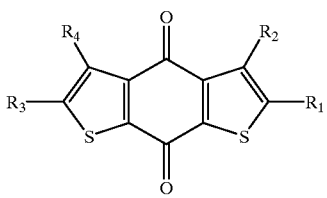

IIa wherein:
$R_1$, $R_2$, $R_3$ and $R_4$ are each independently selected from the group consisting of:
hydrogen, alkyl, carboxy, alkoxy, hydroxyalkyl, alkylcarbonyl, alkylcarbonyloxy, alkyl substituted with alkylcarbonyloxy, thiophenylcarbonyl; nitro and cyano;
thiophenyl and thiophenylthiophenyl, each of which may be unsubstituted or substituted with alkyl, carboxy, alkoxy, hydroxyalkyl, alkylcarbonyl, alkylcarbonyloxy, alkyl substituted with alkylcarbonyloxy, nitro or cyano;
subject to the proviso that at least one of $R_1$, $R_2$, $R_3$ and $R_4$ is not hydrogen;
and the pharmaceutically acceptable salts thereof.

Additional examples of compounds of Formulas I and II are compounds of Formula Ib and compounds of Formula IIb:

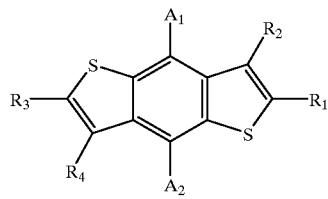

Ib

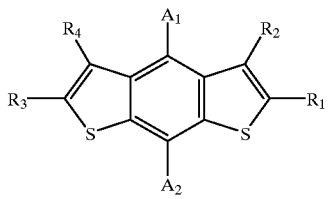

IIb wherein:
$R_1$, $R_2$, $R_3$ and $R_4$ are each independently selected from the group consisting of:
hydrogen, alkyl, carboxy, alkoxy, hydroxyalkyl, alkylcarbonyl, alkylcarbonyloxy; alkyl substituted with alkylcarbonyloxy, thiophenylcarbonyl, nitro and cyano;
thiophenyl and thiophenylthiophenyl, each of which may be unsubstituted or substituted with alkyl, carboxy, alkoxy, hydroxyalkyl, alkylcarbonyl, alkylcarbonyloxy, alkyl substituted with alkylcarbonyloxy, nitro or cyano;
subject to the proviso that at least one of $R_1$, $R_2$, $R_3$ and $R_4$ is not hydrogen;
$A_1$ and $A_2$ are each selected from the group consisting of alkyl, alkoxy, and alkylcarbonyloxy;
and the pharmaceutically acceptable salts thereof.

Thiophenyl and thiophenylthiophenyl substituents that may be used to carry out the present invention include those having the structures:

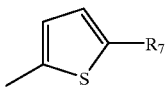 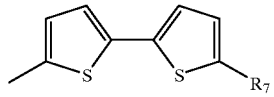

where $R_7$ is the same as given in connection with $R_1$ through $R_4$ above.

Compounds illustrative of Formulas I and II above (along with the reference numbers assigned to these compounds in Examples 1–13 below), are:

2-Acetyl-4,8-dihydrobenzo[1,2-b:4,5-b']dithiophene-4,8-dione (9);

2-(1'-Hydroxyethyl)-4,8-dihydrobenzo[1,2-b:4,5-b']dithiophene-4,8-dione (10);

2-(1'-Acetoxyethyl)-4,8-dihydrobenzo[1,2-b:4,5-b']dithiophene-4,8-dione (11);

2,7-Diacetyl-4,8-dihydrobenzo[1,2-b:4,5-b']dithiophene-4,8-dione (13);

2,7-Bis(1'-hydroxyethyl)-4,8-dihydrobenzo[1,2-b:4,5-b']dithiophene-4,8-dione (14);

2,7-Bis(1'-acetoxyethyl)-4,8-dihydrobenzo[1,2-b:4,5-b']dithiophene-4,8-dione (15);

2-Acetyl-4,8-dihydrobenzo[1,2-b:5,4-b']dithiophene-4,8-dione(19);

2-(1'-Hydroxyethyl)-4,8-dihydrobenzo[1,2-b:5,4-b']dithiophene-4,8-dione (20);

2-(1'-Acetoxyethyl)-4,8-dihydrobenzo[1,2-b:5,4-b']
dithiophene-4,8-dione (21);

2,7-Diacetyl-4,8-dihydrobenzo[1,2-b:5,4-b']dithiophene-
4,8-dione (23);

2,7-Bis(1'-hydroxyethyl)-4,8-dihydrobenzo[1,2-b:5,4-b']
dithiophene-4,8-dione (24);

2,7-Bis(1'-acetoxyethyl)-4,8-dihydrobenzo[1,2-b:5,4-b']
dithiophene-4,8-dione (25).

Compounds of Formula III (along with the numbers assigned to these compounds in Examples 14–16 below) are as follows:

2-Acetyl-naphtho[2,3-b]thiophene-4,9-dione (5);

3-Acetyl-naphtho[2,3-b]thiophene-4,9-dione (6);

7-Acetyl-naphtho[2,3-b]thiophene-4,9-dione (7);

2,7-Diacetyl-naphtho[2,3-b]thiophene-4,9-dione (9);

3,7-Diacetyl naphtho[2,3-b]thiophene-4,9-dione (10).

Additional compounds illustrative of Formulas I and II above are as follows:

| Compound structure |
|---|
| 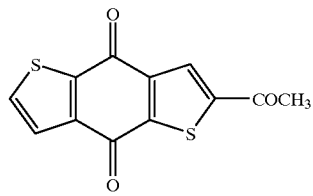 |
| 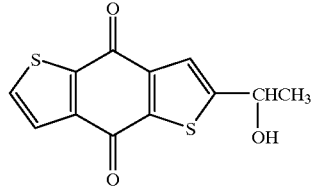 |
| 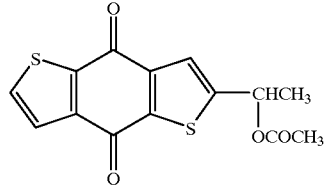 |
| 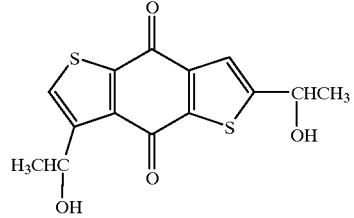 |
| 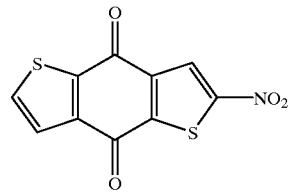 |

-continued

| Compound structure |
|---|
| 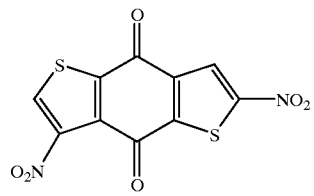 |
| 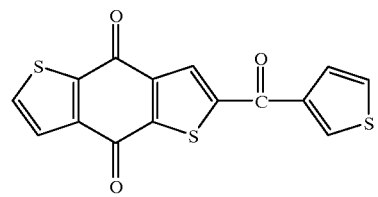 |
| 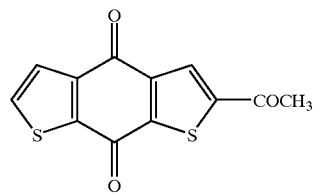 |
| 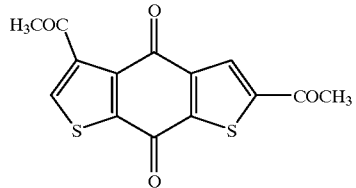 |
| 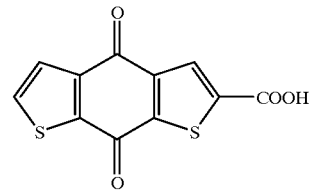 |
| 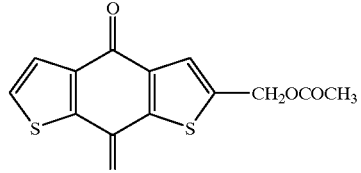 |

The compounds of Formula I, II and III (hereinafter referred to along with their pharmaceutically acceptable salts as "active compounds") are useful as pharmaceutically active agents. The active compounds may be formulated for administration for the treatment of a variety of conditions. In the manufacture of a pharmaceutical formulation according to the invention, the actove compounds including the physiologically acceptable salts thereof, or the acid derivatives of either thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bistris buffer (pH 6) or ethanol/water and contain from 0.1 to 0.2M active ingredient.

The active compounds inhibit tubulin polymerization and have antimitotic activity. Such compounds are useful for the treatment of conditions including psoriasis, gout, papiloma, warts, and various tumors including but not limited to non-small cell lung cancer, colon cancer, central nervous system cancers, melanoma, ovarian cancer, prostate cancer and breast cancer.

Subjects to be treated by the methods of the present invention are typically human subjects although the methods of the present invention may be useful with any suitable subjects known to those skilled in the art, and particularly mammalian subjects including, in addition to humans, horses, cows, dogs, rabbits, fowl, sheep, and the like, for veterinary purposes. As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The following Examples are provided to further illustrate the present invention, and should not be construed as limiting thereof. All melting points were determined on a Yanaco MP-500D apparatus and are uncorrected. IR spectra were recorded on Shimadzu IR-440 and Nicolet Impact 400 FT-IR spectrophotometers as KBr pellets. NMR spectra were obtained on Bruker ARX300 FT-NMR and Varian VXR-300 FT-NMR spectrometers with tetramethylsilane (TMS) as an internal standard. The chemical shift values are expressed in δ values (parts per million). The following abbreviations are used: s=singlet, d=doublet, t=triplet, q=quartet, m=multiplet, and br=broad. Mass spectra (MS) were measured with HP 5995 GC-MS and JEOL JMS-Hx 110 spectrometers. Ultraviolet spectra were recorded on a Shimadzu UV-160A spectrophotometer. Elemental analyses were performed by National Cheng Kung University and National Chung Hsing University, Taiwan. Flash column chromatography was performed on silica gel (mesh 25–150 $\mu$m). Precoated silica gel plates (Kieselgel 60 $F_{254}$ 0.25 mm, Merck) were used for TLC analysis. In these examples, "g" means grams, "mg" means milligrams, "mL" means milliliters, "min." means minute(s), "° C." means degrees Centigrade.

EXAMPLES 1–13

Synthesis and Cytotoxicity of 2-Acetyl-4,8-dihydrobenzo-[1,2-b:4,5-b'] and -[1,2-b:5,4-b'] dithiophene-4,8-dione Derivatives These examples describe synthesis and cytotoxic evaluation of two related series containing two thiophene rings: 4,8-dihydrobenzo[1,2-b:4,5-b']dithiophene-4,8-diones (6, 9–11, 13–15) and 4,8-dihydrobenzo[1,2-b:5,4-b'] dithiophene-4,8-diones (16, 19–21, 23–25). Compounds with the indicated structures are as follows:

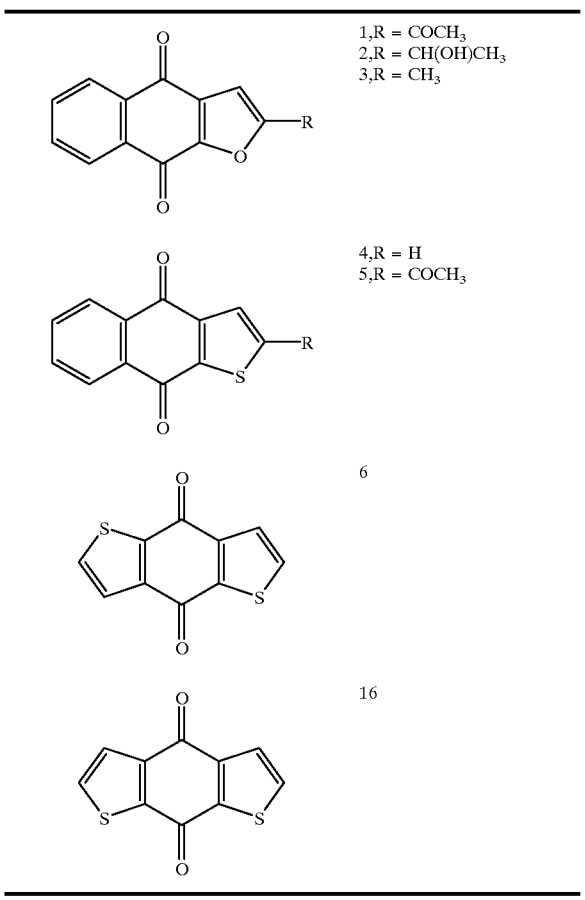

The syntheses of mono- and di-substituted compounds are outlined in Huang, L. J.; Kuo, S. C.; Perng, C. Y.; Chao, Y. H.; Wu, T. S.; McPhail, A. T.; Cheng, H. H.; Lee, K. H. Bioorg & Med. Chem. Letters, submitted. Syntheses of the starting materials, 4-acetoxybenzo-[1,2-b:4,5-b']dithiophene (7) and [1,2-b:5,4-b']dithiophene (17), have been previously described (MacDowell, D. W. H.; Wisowaty, James C. J. Org. Chem. 1971, 36, 4004–4012; MacDowell, D. W. H.; Wisowaty, James C. J. Org. Chem. 1972, 37, 1712–1717). In brief, the former was prepared in 4 steps from 2,3-dibromothiophene and thiophencarboxaldehyde, and the latter was prepared in three steps from 3-bromothiophene and 2-chloromethylthiophene (MacDowell, D. W. H.; Wisowaty, James C. J. Org. Chem. 1972, 37, 1712–1717). Friedel-Crafts acylation of 7 or 17 with two equivalents of acetyl chloride and AlCl$_3$ gave intermediates 8 and 18, respectively. CrO$_3$ oxidation in HOAc then gave 9 or 19. In their $^1$H NMR spectra, each compound showed one CH$_3$ singlet at ca. 2.67 ppm, AB-type signals at ca. 7.68 and 7.74 ppm, and a singlet at ca. 8.12 ppm. From these data together with the $^{13}$C NMR and mass spectral results, both 9 and 19 appeared to be monoacetyl derivatives, with the position of substitution either at C-2 or C-3. X-ray crystallography confirmed both to be the 2-acetyl derivative. Reduction with NaBH$_4$ in MeOH gave the secondary alcohols 10 and 20 in each series, and acetylation of these compounds with acetyl chloride gave the expected 11 and 21.

A diacetyl derivative in each dithiophene series was prepared by Friedel Crafts acetylation (20 equivalents) of 7 and 17 to give 12 and 22, followed by CrO$_3$ oxidation to give 13 and 23. Three structures are possible for each product: two symmetric (for 13; 3,7- or 2,6-disubstituted and for 23; 3,5- or 2,6-disubstituted) and one asymmetric (for 13; 2,7-disubstituted and for 23; 2,5-disubstituted). In each case (data given only for 13), because the IR spectrum showed three carbonyl absorptions (1670, 1675, and 1695 cm$^{-1}$), the $^1$H-NMR spectrum showed two methyl singlets (2.66 and 2.67 ppm) and non-equivalent aromatic signals (7.91 and 8.11 ppm), and the $^{13}$C-NMR spectrum showed four carbonyl signals (173.8, 174.0, 190.6, and 196.9 ppm), the two symmetric structures were ruled out. Thus, in both dithiophene series, acetylation occurred first at C-2, then at the carbon beta to the second sulfur atom giving, after oxidation, 2,7-diacetyl-4,8-dihydrobenzo[1,2-b:4,5-b'] dithiophene-4,8-dione (13) and 2,5-diacetyl-4,8-dihydrobenzo [1,2-b:5,4-b']dithiophene-4,8-dione (23). Reduction followed by acetylation of 13 and 23 then gave 14 and 24, respectively, followed by acetylation to 15 and 25, respectively.

Scheme 1.
Synthesis of derivatives 9–11 and 13–15.

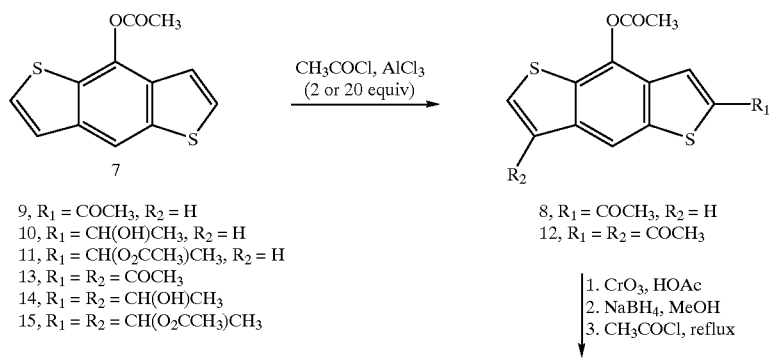

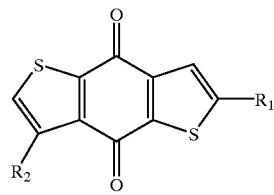

Scheme 2.
Synthesis of derivatives 19–21 and 23–25.

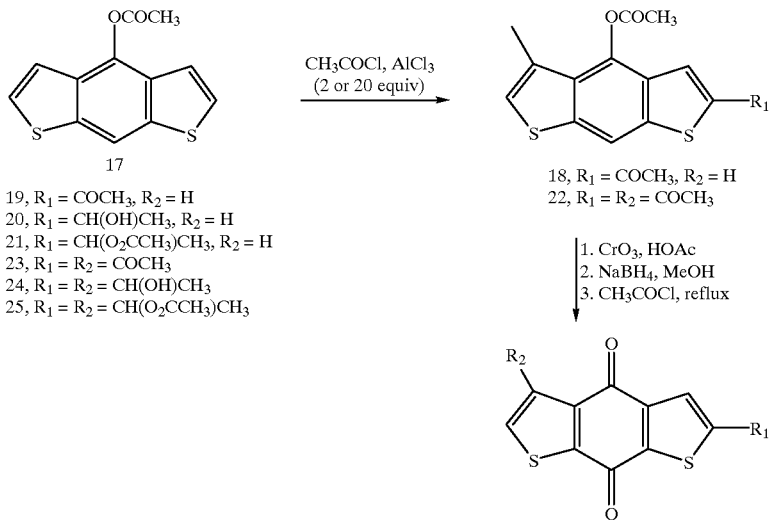

19, R₁ = COCH₃, R₂ = H
20, R₁ = CH(OH)CH₃, R₂ = H
21, R₁ = CH(O₂CCH₃)CH₃, R₂ = H
23, R₁ = R₂ = COCH₃
24, R₁ = R₂ = CH(OH)CH₃
25, R₁ = R₂ = CH(O₂CCH₃)CH₃

18, R₁ = COCH₃, R₂ = H
22, R₁ = R₂ = COCH₃

1. CrO₃, HOAc
2. NaBH₄, MeOH
3. CH₃COCl, reflux

Example 1

2-Acetyl-4,8-dihydrobenzo[1,2-b:4,5-b']dithiophene-4,8-dione (9)

To a stirring mixture of acetyl chloride (5.1 g, 65 mmol) and AlCl₃ (8.7 g, 65 mmol) in 1,2-dichloroethane (200 mL) under N₂ was added dropwise a solution of 4-acetoxybenzo[1,2-b:4,5-b']dithiophene (7)[7a] (8 g, 32.3 mmol) in 1,2-dichloroethane (90 mL). After stirring for 4 h, this solution was poured into dilute HCl and the aqueous layer was extracted with CHCl₃ three times. The combined extracts were washed with saturated NaHCO₃ and water, dried over anhydrous MgSO₄, and concentrated under reduced pressure to give 7.5 g of the crude intermediate 4-acetoxy-2-acetylbenzo[1,2-b;4,5-b']dithiophene (8).

To a suspension of crude 8 (7.5 g) in HOAc (30 mL) was added CrO₃ (5.7 g, 57 mmol). After stirring for 1 h, i-PrOH (20 mL) and CHCl₃ (300 mL) were added and stirred for 30 min. The resulting solution was poured into ice water, and the aqueous layer was extracted with CHCl₃ three times. The combined extracts were dried over anhydrous MgSO₄ and concentrated under reduced pressure. The residue was purified by column chromatography (silica gel, CHCl₃) to give 9 (mp 223–225 °C.) in a 45% yield. IR (KBr) 1650, 1670 (C=O) cm⁻¹; ¹H NMR (CDCl₃) δ 2.67 (s, 3H, CH₃), 7.68 (d, J=5.1 Hz, 1H, H-7), 7.74 (d, J=5.1 Hz, 1H, H-6), 8.12 (s, 1H, H-3); ¹³C NMR (CDCl₃): δ 26.9 (C-2-CH₃), 126.9 (C-7), 129.4 (C-3), 134.3 (C-6), 170.0 (C-4), 174.4 (C-8), 190.7 (C-2-C=O); MS m/z 262 (M⁺); Anal. (C₁₂H₆O₃S₂) C, H.

Example 2

2-Acetyl-4,8-dihydrobenzo[1,2-b:5,4-b']dithiophene-4,8-dione(19)

This compound was prepared in an analogous manner from 4-acetoxybenzo[1,2-b:5,4-b']dithiophene (18). Yield 35%; mp 173–175° C.; UV (CH₂Cl₂) λ$_{max}$ 277 (log ε 4.44); IR (KBr) 1663 (C=O) cm⁻¹; ¹H NMR (CDCl₃) δ 2.66 (s, 3H, CH₃), 7.67 (d; J=5.1 Hz, 1H, H-5), 7.76 (d, J=5.1 Hz, 1H, H-6), 8.11 (s, 1H, H-3); ¹³C NMR (CDCl₃) δ 26.8 (C-2-CH₃), 126.9 (C-5), 129.4 (C-3), 134.6 (C-6), 150.1 (C-2), 172.9 (C-4), 175.2 (C-8), 190.4 (C-2-C=O); MS m/z 262 (M⁺); Anal. (C₁₂H₆O₃S₂) C, H.

Example 3

2-(1'-Hydroxyethyl)-4,8-dihydrobenzo[1,2-b:4,5-b'] dithiophene-4,8-dione (10)

To a suspension of 9 (3.0 g, 11.2 mmol) in MeOH (200 mL) was added NaBH₄ (1.5 g, 39.7 mmol) and stirring continued for 2 h. After acidification with dilute HCl, the solution was extracted with CHCl₃. The organic fraction was washed with water, dried, and condensed. The residue was purified by column chromatography (silica gel, CHCl₃) to give 10 as a yellow solid (mp 166–168° C.) in a 93% yield. IR (KBr) 1650, 1680 (C=O), 3200–3600 (OH) cm⁻¹; ¹H NMR (DMSO-d₆) δ 1.48 (d, J=6.3 Hz, 3H, CH₃), 5.02–5.07 (m, 1H, CH), 6.10 (d, J=4.8 Hz, 1H, OH), 7.45 (s, 1H, H-3), 7.62 (d, J=5.1 Hz, 1H, H-7), 8.15 (d, J=5.1 Hz, 1H, H-6); ¹³C NMR (DMSO-d₆): δ 25.3 (C-2-CH₃), 64.6 (C-2-CH), 120.7 (C-3), 126.1 (C-7), 135.5 (C-6), 163.0 (C-2), 174.0, 174.4 (C-4, C-8); MS m/z 264 (M⁺); Anal. (Cl₂H₈O₃S C, H.

Example 4

2-(1'-Hydroxyethyl)-4,8-dihydrobenzo[1,2-b:5,4-b']dithiophene-4,8-dione (20)

Compound 19 was reduced in a similar manner to give compound 20. Yield 85%; mp 170–172° C.; UV (CHCl$_3$) $\lambda_{max}$ 238 (log $\epsilon$ 4.35), 294 (log $\epsilon$ 4.21); IR (KBr) 1655, 1663 (C=O), 3100–3500 (OH) cm$^{-1}$; $^1$H NMR (CDCl$_3$) $\delta$ 1.65 (d, J=6.5 Hz, 3H, CH$_3$), 5,16–5.21 (m, 1H, CH), 7.43 (s, 1H, H-3), 7.60 (d, J=5.1 Hz, 1H, H-5), 7.66 (d, J=5.1 Hz, 1H, H-6); $^{13}$C NMR (CDCl$_3$) $\delta$ 25.3 (C-2-CH$_3$), 66.5 (C-2-CH), 121.8 (C-3), 126.6 (C-5), 133.4 (C-6), 160.0 (C-2), 173.1 (C-4), 176.0 (C-8); MS m/z 264 (M$^+$); Anal. (C$_{12}$H$_8$O$_3$S$_2$) C, H.

Example 5

2-(1'-Acetoxyethyl)-4,8-dihydrobenzo[1,2-b:4,5-b']dithiophene-4,8-dione (11)

Acetyl chloride (1.1 g, 13.6 mmol) was added to a solution of 10 (2.0 g, 7.4 mmol) in 1,2-dichloroethane (100 mL) and the mixture was refluxed for 4 h. After this time, the solution was poured into ice water. The organic layer was separated, washed with saturated NaHCO$_3$ and water, dried, and evaporated. The residue was subjected to column chromatography (silica gel, C$_6$H$_6$) to give 11 as a yellow solid (mp 174–176° C.) in a 74% yield: IR (KBr) 1645, 1655, 1724 (C=O) cm$^{-1}$; $^1$H NMR (CDCl$_3$) $\delta$ 1.68 (d, J=6.6 Hz, 3H, CHCH$_3$), 2.13 (s, 3H, COCH$_3$), 6.10–6.17 (q, J=6.6 Hz, 1H, CH), 7.53 (s, 1H, H-3), 7.63 (d, J=5.1 Hz, 1H, H-7), 7.68 (d, J=5.1 Hz, 1H, H-6); $^{13}$C NMR (CDCl$_3$): $\delta$ 21.0 (C-2-COCH$_3$), 22.0 (C-2-CHCH$_3$), 67.4 (C-2-CH), 123.4 (C-3), 126.6 (C-7), 133.6 (C-6), 154.0 (C-2), 174.4×2 169.8 (C-2-C=O), (C-4, C-8); MS m/z 306 (M$^+$); Anal. (C$_{14}$H$_{10}$O$_4$S$_2$) C, H.

Example 6

2-(1'-Acetoxyethyl)-4,8-dihydrobenzo[1,2-b:5,4-b']dithiophene-4,8-dione (21)

Compound 21 was prepared by acetylation of 20 in an analogous manner. Yield 68%; mp 165–166° C.; UV (CH$_2$Cl$_2$) $\lambda_{max}$ 239 (log $\epsilon$ 4.33), 294 (log $\epsilon$ 4.23); IR (KBr) 1670, 1750 (C=O) cm$^{-1}$; $^1$H NMR (CDCl$_3$) $\delta$ 1.69 (d, J=6.6 Hz, 3H, CHCH$_3$), 2.11 (s, 3H, COCH$_3$), 6.08–6.15 (q, J=6.6 Hz, 1H, CH), 7.49 (s, 1H, H-3), 7.58 (d, J=5.1 Hz, 1H, H-5), 7.67 (d, J=5.1 Hz, 1H, H-6); $^{13}$C NMR (CDCl$_3$) $\delta$ 21.0 (C-2-COCH$_3$), 21.9 (C-2-CHCH$_3$), 67.3 (C-2-CH), 123.6 (C-3), 126.7 (C-5), 133.6 (C-6), 154.0 (C-2), 169.8 (C-2-C=O), 172.9 (C-4), 175.6 (C-8); MS m/z 324 (M+NH$_4$+NH$_4$$^+$); Anal. (C$_{14}$H$_{10}$O$_4$S$_2$) C, H.

Example 7

2,7-Diacetyl-4,8-dihydrobenzo[1,2-b:4,5-b']dithiophene-4,8-dione (13)

Compound 7 was converted first to 12 then to 13 using similar reaction conditions as for the synthesis of 9 from 7. The molar equivalents of acetyl chloride and AlCl$_3$ were increased to 20. Column chromatography on silica gel eluting with CHCl$_3$:EtOH (100:1) gave 13 (mp 207–208° C.) in a 41% yield. UV $\lambda_{max\ (CHCl3)}$ 279 (log $\epsilon$ 3.43); IR (KBr) 1670, 1675, 1695 (C=O) cm$^{-1}$; $^1$H NMR (CDCl$_3$) $\delta$ 2.66 (s, 3H, C-7-CH$_3$), 2.67 (s, 3H, C-2-CH$_3$), 7.91 (s, 1H, H-3), 8.11 (s, 1H, H-6); $^{13}$C NMR (DMSO-d$_6$) $\delta$ 26.7 (C-2-CH$_3$), 30.4 (C-7-CH$_3$), 130.0 (C-3), 135.4 (C-6), 173.5 (C-4), 173.8 (C-8); 191.4 (C-2-C=O), 196.7 (C-7-C=O); MS m/z 304 (M$^+$); Anal. (C$_{14}$H$_8$O$_4$S$_2$) C, H.

Example 8

2,7-Diacetyl-4,8-dihydrobenzo[1,2-b:5,4-b']dithiophene-4,8-dione (23)

Compound 17 was converted in two steps to 23 as detailed in the above procedure. Yield 32%; mp 190–192° C.; UV (CH$_2$Cl$_2$) $\lambda_{max}$ 226 (log $\epsilon$ 3.99), 275 (log $\epsilon$ 3.96); IR (KBr) 1650, 1676, 1689 (C=O) cm$^{-1}$; $^1$H NMR (CDCl$_3$) $\delta$ 2.66 (s, 3H, C-5-CH$_3$), 2.67 (s, 3H, C-2-CH$_3$), 7.81 (s, 1H, H-6), 8.07 (s, 1H, H-3); $^{13}$C NMR (CDCl$_3$) $\delta$ 26.9 (C-2-CH$_3$), 30.6 (C-5-CH$_3$), 129.7 (C-3), 135.0 (C-6), 147.9 (C-5), 150.7 (C-2), 172.8 (C-4), 175.0 (C-8), 190.6 (C-2-C=O); MS m/z 304 (M$^+$); Anal. (C$_{14}$H$_8$O$_4$S$_2$) C, H.

Example 8

2,7-Bis(1'-hydroxyethyl)-4,8-dihydrobenzo [1,2-b:4,5-b']dithiophene-4,8-dione (14)

Compound 13 was reduced with NaBH$_4$ as in the preparation of 10. Column chromatography on silica gel eluting with CHCl$_3$:MeOH (100:1) gave 14 as a yellow solid (mp 218–219° C.) in a 90% yield. IR (KBr) 1650, 1670 (C=O), 3100–3500 (OH) cm$^{-1}$; $^1$H NMR (DMSO-d$_6$) $\delta$ 1.36 (d, J=6.0 Hz, 3H, C-7-CH$_3$), 1.48 (d, J=6.0 Hz, 3H, C-2-CH$_3$), 5.05 (s, 1H, C-2-OH), 5.33 (s, 1H, C-7-OH), 5.52 (m, 1H, C-7-CH), 6.17 (m, 1H, C-2-CH), 7.41 (s, 1H, H-3), 7.97 (s, 1H, H-6); $^{13}$C NMR (DMSO-d$_6$) $\delta$ 24.8 (C-7-CH$_3$), 25.5 (C-2-CH$_3$), 64.1 (C-7-CH), 64.9 (C-2-CH), 120.7 (C-3), 130.1 (C-6), 174.7 (C-4), 175.3 (C-8); MS m/z 308 (M$^+$); Anal. (C$_{14}$H$_{12}$O$_4$S$_2$) C, H.

Example 9

2,7-Bis(1'-hydroxyethyl)-4,8-dihydrobenzo[1,2-b:5,4-b']dithiophene-4,8-dione (24)

Compound 23 was reacted in a similar manner as for 14 to give 24. Yield 85%; mp 218–220° C.; UV (CH$_2$Cl$_2$) $\lambda_{max}$ 241 (log $\epsilon$ 4.51); IR (KBr) 1650, 1670 (C=O), 3100–3500 (OH) cm$^{-1}$; $^1$H NMR (CDCl$_3$) $\delta$ 1.65 (d, J=6.6 Hz, 3H, C-2-CH$_3$), 1.98 (d, J=6.6 Hz, 3H, C-5-CH$_3$), 5.16–5.21 (m, 1H, C-2-CH), 5.30–5.35 (m, 1H, C-5-CH), 7.43 (s, 1H, H-3), 7.56 (s, 1H, H-6); $^{13}$C NMR (CDCl$_3$) $\delta$ 25.6 (C-2-CH$_3$), 26.6 (C-5-CH$_3$), 52.2 (C-5-CH), 65.0 (C-2-CH), 122.0 (C-3), 123.8 (C-6), 155.8 (C-5), 160.0 (C-2), 173.0 (C-4), 175.6 (C-8); MS m/z 308 (M$^+$); Anal. (C$_{14}$H$_{12}$O$_4$S$_2$) C, H.

Example 10

2,7-Bis(1'-acetoxyethyl)-4,8-dihydrobenzo[1,2-b:4,5-b']dithiophene-4,8-dione (15)

Compound 15 was prepared from 14 in an identical manner to that compound 11. Yield 72%; yellow solid; mp 180–182° C.; UV (CHCl$_3$) $\lambda_{max}$ 245 (log $\epsilon$ 4.32); IR (KBr) 1640, 1720 (C=O) cm$^{-1}$; $^1$H NMR (CDCl$_3$) $\delta$ 1.58 (d, J=6.6 Hz, 3H, C-7-CHCH$_3$), 1.67 (d, J=6.6 Hz, 3H, C-2-CHCH$_3$), 2.12 (s, 6H, COCH$_3$×2), 6.10–6.16 (q, J=6.6 Hz, 1H, C-2-CH), 6.50–6.56 (q, J=6.6 Hz, 1H, C-7-CH), 7.50 (s, 1H, H-3), 7.62 (s, 1H, H-6); $^{13}$C NMR (CDCl$_3$): $\delta$ 21.0, 21.1, 21.3, 22.0 (CH$_3$×4), 67.4, 67.8 (CH×2), 123.2 (C-3), 128.6 (C-6), 154.0 (C-7), 154.1 (C-2), 169.6, 169.7 (C-2-C=O, C-7-C=O), 174.3, 174.8 (C-4, C-8); MS m/z 392 (M$^+$); Anal. (C$_{18}$H$_{16}$O$_6$S$_2$) C, H.

Example 11

2,7-Bis(1'-acetoxyethyl)-4,8-dihydrobenzo[1,2-b:5,4-b']dithiophene-4,8-dione (25)

Compound 24 was acetylated in a similar manner as given above to produce 25. Yield 68%; mp 172–174° C.; UV (CH$_2$Cl$_2$) $\lambda_{max}$ 226 (log ε 4.10); IR (KBr) 1663, 1655 (C=O) cm$^{-1}$; $^1$H NMR (CDCl$_3$) δ 1.58 (d, J=6.6 Hz, 3H, C-5-CHCH$_3$), 1.68 (d, J=6.6 Hz, 3H, C-2-CHCH$_3$), 2.12 (s, 6H, COCH$_3$×2), 6.10–6.17 (q, J=6.6 Hz, 1H, C-2-CH), 6.50–6.57 (q, J=6.6 Hz, 1H, C-5-CH), 7.51 (s, 1H, H-3), 7.63 (s, 1H, H-6); $^{13}$C NMR (CDCl$_3$): δ 21.0, 21.2, 21.3, 22.0 (CH$_3$×4), 67.4 (C-2-CH), 67.8 (C-5-CH), 123.8 (C-3), 128.7 (C-6), 146.5 (C-5), 154.3 (C-2), 169.8×2 (C-2-C=O, C-5-C=O), 172.9 (C-4), 176.2 (C-8); MS m/z 391 (M$^+$-1); Anal. (C$_{18}$H$_{16}$O$_6$S$_2$) C, H.

Example 12

Elemental Analyses

9: Calcd: C, 54.97; H, 2.31. Found: C, 54.75; H, 2.38%.
10: Calcd: C, 54.55; H, 3.05. Found: C, 54.34, H, 2.97%.
11: Calcd: C, 54.90; H, 3.29. Found: C, 54.79; H, 3.40%
13: Calcd: C, 55.27; H, 2.65. Found: C, 55.25; H, 2.61%.
14: Calcd: C, 54.54; H, 3.93. Found: C, 54.60; H, 3.97%.
15: Calcd: C, 55.10; H, 4.11. Found: C, 55.01; H, 4.13%.
19: Calcd: C, 54.97; H, 2.31. Found: C, 54.84; H, 2.33%.
20: Calcd: C, 54.55; H, 3.05. Found: C, 54.45, H, 3.08%.
21: Calcd:.C, 54.90; H, 3.29. Found: C, 54.80; H, 3.18%.
23: Calcd: C, 55.27; H, 2.65. Found: C, 55.30; H, 2.49%.
24: Calcd: C, 54.54; H, 3.93. Found: C, 54.31; H, 3.98%.
25: Calcd: C, 55.10; H, 4.11. Found: C, 54.98; H, 4.05%.

Example 13

Activity of Compounds

In preliminary testing, the unsubstituted parent compounds 6 and 16 showed significant activity against several leukemia cell lines (see Table 1).

TABLE 1

Cytotoxicity of 6 and 16 against Leukemia Cell Lines

| Cell Line | IC$_{50}$ (μg/Ml) 6 | IC$_{50}$ (μg/Ml) 16 |
|---|---|---|
| KB | 0.058 | 0.05 |
| HCT-8 | 0.06 | 0.032 |
| P-399 | <0.1 | — |
| L-1210 | 0.32 | — |
| A549 | 0.048 | 0.032 |
| CAKI-1 | 0.28 | 0.11 |
| SK-MEL-2 | — | 0.06 |
| MCF-7 | 0.09 | <0.016 |

Therefore, the substituted compounds 9–11, 13–15 and 19–21, 23–25 were submitted to NCI for in vitro testing against 58 human tumor cell lines derived from leukemia, small and non-small cell lung cancers, colon cancer, CNS cancer, melanoma, ovarian cancer, renal cancer, and breast cancer in accordance with known techniques (Paull, K. D.; Shoemaker, R. H.; Hodes, L.; Monks, A.; Scudiero, D. A.; Rubinstein, L.; Plowman, J.; Boyd, M. R. *J. Natl. Cancer Inst.* 1989, 81, 1088–1092; Monks, A.; Scudiero, D.; Skehan, P.; Shoemaker, R.; Paull, K.; Vistica, D.; Hose, C.; Langley, J.; Cronise, P.; Vaigro-Woiff, A.; Gray-Goodrich, M.; Campbell, H.; Mayo, J.; Boyd, M. *J. Natl. Cancer Inst.* 1991, 83, 757–766; Boyd, M. R.; Paull, K. D.; Rubinstein, L. R.; Valeriote, F. A.; Corbett, T., Baker, L., Eds.; Kluwer Academic Publishers; Amsterdam, 1992, 11–34). All compounds were active against all cell lines with mean log GI$_{50}$ values ranging from −5.92 (compound 15) to −7.40 (compound 11). (Activity is defined as log GI$_{50}$<−4 where GI$_{50}$ is the molar concentration causing 50% cell growth inhibition). Table 2 shows the biological data in selected cell lines.

TABLE 2

Inhibition of In Vitro Cancer Cell Lines by Disubstituted Dihydrobenzothiophenediones Cytotoxicity log GI$_{50}$ (M)[a,b]

| Cell Line | 9 | 10 | 11 | 13 | 14 | 15 | 19 | 20 | 21 | 23 | 24 | 25 |
|---|---|---|---|---|---|---|---|---|---|---|---|---|
| Melanoma | | | | | | | | | | | | |
| LOX IMVI | −7.60 | −8.00 | <−8.00 | −5.98 | −7.26 | −5.80 | <−8.00 | −7.62 | −6.68 | −7.65 | −6.92 | −6.93 |
| MALME-3M | −6.93 | −7.80 | <−8.00 | −5.88 | −7.56 | −6.73 | −7.79 | −7.72 | −6.92 | −6.65 | −6.82 | −6.88 |
| M14 | −6.89 | −7.83 | −7.89 | −5.82 | −7.24 | −6.29 | −7.76 | −7.83 | −6.79 | −6.36 | −6.81 | −6.94 |
| SK-MEL-2 | −6.69 | −7.04 | −7.58 | −5.76 | −6.95 | −5.81 | −7.48 | −7.51 | −6.38 | −6.79 | −6.69 | −6.82 |
| SK-MEL-28 | −6.80 | −7.76 | −7.72 | −5.75 | −6.73 | −5.78 | <−8.00 | −7.41 | −6.19 | −6.69 | −6.63 | −6.68 |
| SK-MEL-5 | −7.63 | <−8.00 | −7.87 | −5.92 | −7.90 | −6.20 | <−8.00 | −7.87 | −6.97 | −6.50 | −6.85 | −7.47 |
| UACC-257 | −6.90 | −7.84 | −7.60 | −6.25 | −7.21 | −6.20 | −7.86 | −7.74 | −6.67 | −6.78 | −6.79 | −6.76 |
| UACC-62 | −6.68 | −7.79 | −7.77 | −5.71 | −7.49 | −5.96 | −7.77 | −7.65 | −5.86 | −6.63 | −6.61 | −6.70 |
| Leukemia | | | | | | | | | | | | |
| HL-60(TB) | −7.35 | −7.84 | <−8.00 | −7.28 | −7.95 | −7.17 | — | −7.16 | −5.76 | — | −6.36 | −6.19 |
| Non-Small Cell Lung Cancer | | | | | | | | | | | | |
| NCI-H23 | −6.82 | −7.84 | −7.95 | −5.88 | −7.47 | −6.06 | −7.74 | −7.81 | −6.66 | −6.54 | −6.72 | −6.80 |
| NCI-H522 | −6.80 | −6.93 | −6.83 | −6.28 | −6.52 | — | −7.76 | −6.91 | −6.06 | −6.42 | −6.40 | −6.71 |
| Ovarian Cancer | | | | | | | | | | | | |
| OVCAR-3 | −6.81 | −7.62 | <−8.00 | −6.64 | −7.93 | −6.56 | <8.00 | −6.93 | −6.31 | −7.53 | −6.44 | −6.57 |
| OVCAR-8 | −6.53 | −6.71 | −7.44 | −5.84 | −6.66 | −6.34 | −7.51 | −6.79 | −5.85 | −6.64 | −6.58 | −6.63 |

TABLE 2-continued

Inhibition of In Vitro Cancer Cell Lines by
Disubstituted Dihydrobenzothiophenediones

| | Cytotoxicity log $GI_{50}$ (M)[a,b] | | | | | | | | | | | |
|---|---|---|---|---|---|---|---|---|---|---|---|---|
| Cell Line | 9 | 10 | 11 | 13 | 14 | 15 | 19 | 20 | 21 | 23 | 24 | 25 |
| Breast Cancer | | | | | | | | | | | | |
| HS 578T | −6.80 | −6.97 | −6.81 | −5.62 | −6.50 | −5.68 | −7.44 | −7.24 | −6.29 | −6.55 | −6.50 | −6.61 |
| MDA-MB-435 | −7.43 | <−8.00 | <−8.00 | −6.75 | −7.75 | −6.73 | <−8.00 | −7.79 | −6.74 | −6.64 | −6.80 | −7.67 |
| MDA-N | −7.43 | −7.88 | <−8.00 | −6.76 | −7.68 | −6.67 | <−8.00 | −7.73 | −7.72 | −6.71 | −6.83 | −7.23 |
| BT-549 | −6.74 | −7.11 | −7.34 | −5.76 | −6.79 | −5.67 | −7.75 | −7.46 | −6.55 | −6.04 | −6.71 | −6.71 |
| Mean Value[c] | −6.38 | −6.97 | −7.40 | −5.93 | −6.83 | −5.92 | −7.33 | −6.87 | −6.10 | −6.47 | −6.32 | −6.63 |

[a]Data obtained from NCI's in vitro disease-oriented tumor cells screen.
[b]Data are an average of at least two testings.
[c]Mean value over all cell lines tested.

In the 4,8-dihydrobenzo[1,2-b:4,5-b']dithiophene-4,8-dione series, the monosubstituted 2-(1'-acetyoxyethyl) compound (11) showed the highest overall potency (mean log $GI_{50}$=−7.40); however, the analogous compound 21 was among the least active in the 4,8-dihydrobenzo[1,2-b:5,4-b']dithiophene-4,8-dione series. In the latter series, the monosubstituted 2-acetyl compound (19) was the most active. In both series, compounds with one hydroxyethyl group (10 and 20) also showed excellent overall cytotoxicity. Only one disubstituted compound 14 [2,7-bis(1'-hydroxyethyl)-4,8-dihydrobenzo[1,2-b:4,5-b']dithiophene-4,8-dione] showed overall cytotoxicity comparable to the monosubstituted compounds.

Compounds 13 and 15, which are disubstituted with acetyl and 1-acetoxyethyl groups, were not selective towards melanoma cell lines and, in general, were less active in all cell lines. The remaining ten compounds showed striking potency towards all melanoma cell lines. Compounds 11 and 19 were the most sensitive with log $GI_{50}$ values ranging from −7.48 to <−8.00 in these cell lines. All compounds including 13 and 15 showed high activity against HL-60(TB) leukemia, OVCAR-3 ovarian cancer, MDA-MB-435 and MDA-N breast cancers.

In summary, in a direct comparison, the monosubstituted compounds, in general, displayed stronger selectivity than the corresponding disubstituted compounds. 2-(1'-Acetoxyethyl)-4,8-dihydrobenzo[1,2-b:4,5-b']dithiophene-4,8-dione (11) and 2-acetyl-4,8-dihydrobenzo[1,2-b:5,4-b'] dithiophene-4,8-dione (19) were the most active compounds tested and are candidates for further in vivo testing.

EXAMPLES 14–16

Synthesis and Cytotoxicity of Acetyl-4H,9H-Naphtho[2,3-b]Thiophene-4,9-Diones Compounds in Examples 14–16 below are numbered separately from those numbered in Examples 1–13 above.

Many anthraquinones, including mitoxantrone (1), show antineoplastic activity (Zee-Cheng, R. Y.; Podrebarac, E. G; Menon, C. S.; Cheng, C. C. J. Med. Chem. 1979, 22, 501–505). In addition, the natural product 2-acetyl-4H, 9H-naphtho[2,3-b]furan-4,9-dione (2) isolated from Tabebuia cassinoids (Lam.) DC. (Bignoniaceae) demonstrated cytotoxicity in the KB cell culture assay ($ED_{50}$ value=4.2 $\mu$M). Accordingly, a third compound, naphtho[2,3-b]thiophene-4,9-dione (3) was evaluated for cytotoxicity against KB cells resulting in $ED_{50}$ value of 6.5 $\mu$M (Goncalves, R.; Brown, E. V. J. Org. Chem. 1952, 17, 698–704; Weinmayr, V. J. Am. Chem. Soc. 1952, 74,.4353–4357; Carruthers, W.; Douglas, A. G.; Hill, J. J. Chem. Soc. 1962, 704–708; Carruthers, W. J. Chem. Soc. 1963, 4477–4483; Tagawa, H.; Ueno, K. Chem. Pharm. Bull. 1978, 26, 1384–1393.).

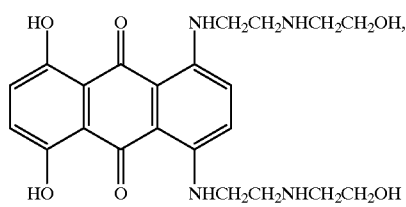

Mitoxantrone

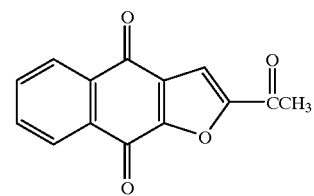

These examples describes the synthesis and cytotoxic evaluation of three mono-(5–7) and two di-(9–10) acetyl substituted derivatives.

Monoacetyl derivatives of 4H, 9H-naphtho[2,3-b] thiophene-4,9-dione (3) were synthesized as shown below. Compound 3 was first reduced by sodium thiosulfate under alkaline conditions, then dimethylsulfate was added giving O-methylation to the expected 4,9-dimethoxynaphtho[2,3-b]thiophene (4).

Compound 4 was reacted in a Friedel-Crafts acetylation with an equal molar ratio of acetyl chloride in the presence of $AlCl_3$, and the reaction product was then oxidized by $CrO_3$. Column chromatography gave three oxidized derivatives: 5 with mp 139–140° C., 6 with mp 244–245° C., and 7 with mp 146–147° C.

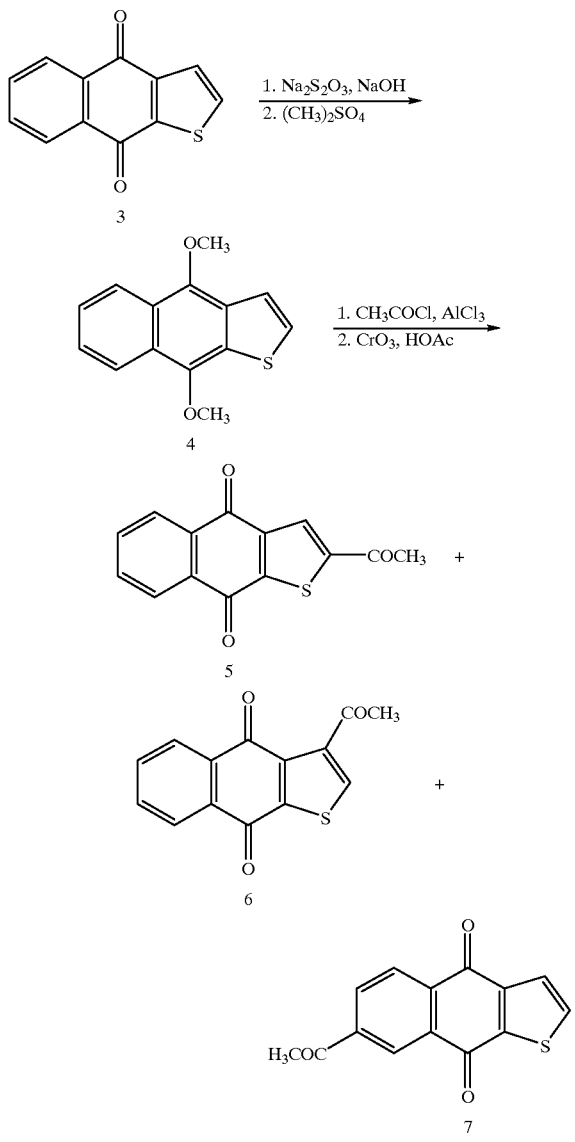

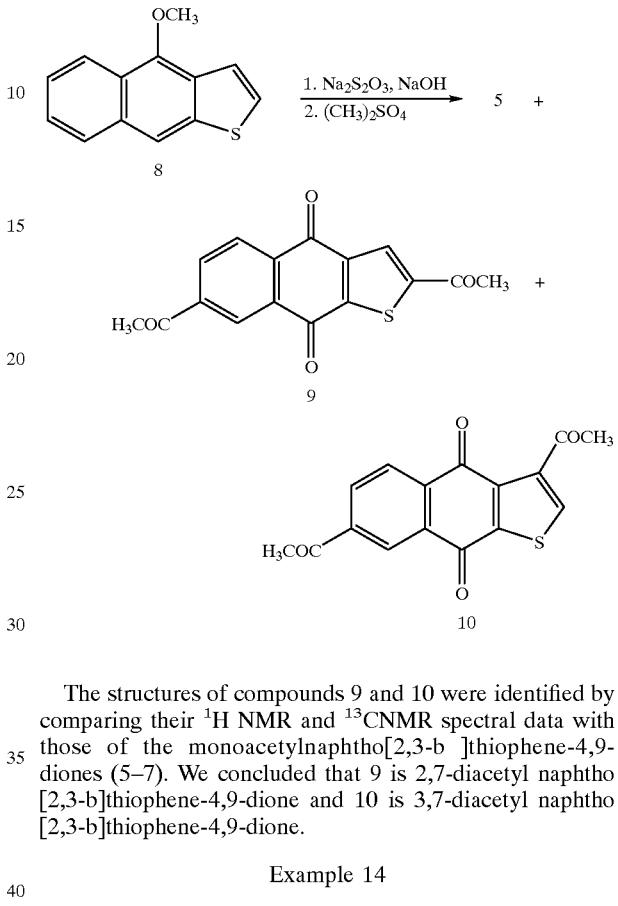

Based on mass spectral [m/z (256, M⁺)] and elemental analysis data, the molecular formulas of all three products were determined as $C_{14}H_8O_3S$, which suggested positional isomers of monoacetylnaphtho[2,3-b]thiophene-4,9-dione. The $^1H$ NMR and $^{13}C$ NMR analysis including two dimensional techniques (i.e. $^1H$-$^1H$ Cosy, HMQC, HMBC) led us to assign compound 5 as 2-acetylnaphtho[2,3-b]thiophene-4,9-dione; this assignment was confirmed by X-ray crystallographic analysis.

Assignments of the $^1H$-NMR and $^{13}C$-NMR spectra of products 6 and 7 were made by comparison with the spectra of compound 3 and by 2D-NMR techniques including $^1H$-$^1H$ Cosy, HMQC and HMBC. From the above data, it was concluded that products 6 and 7 were the 3-acetyl and 7-acetyl derivatives, respectively, of 3.

For the synthesis of diacetyl derivatives of 3, 4-acetoxynaphtho[2,3-b]thiophene (8) was reacted with excess acetyl chloride and AlCl₃, and the resulting reaction products were oxidized with CrO₃ (MacDowell, D. W. H.; Wistowaty, James C. *J. Org. Chem.* 1971, 36, 4004–4012; MacDowell, D. W. H.; Wistowaty, James C. *J. Org. Chem.* 1972, 37, 1712–1717). The monoacetylated 5 was isolated by column chromatography together with two new products: 9 with mp 202–204° C. and 10 with mp 180–182° C. Both compounds were diacetylated as seen from their molecular formula ($C_{16}H_{10}O_4S$) obtained by mass spectroscopy [m/z (298, M⁺)] and elemental analysis.

The structures of compounds 9 and 10 were identified by comparing their $^1H$ NMR and $^{13}C$NMR spectral data with those of the monoacetylnaphtho[2,3-b]thiophene-4,9-diones (5–7). We concluded that 9 is 2,7-diacetyl naphtho[2,3-b]thiophene-4,9-dione and 10 is 3,7-diacetyl naphtho[2,3-b]thiophene-4,9-dione.

Example 14

2-Acetyl-(5), 3-Acetyl-(6), and 7-Acetyl-naphtho[2,3-b]thiophene-4,9-dione (7)

Dimethyl sulfate (7.6 mL, 60 mmol) was added dropwise to a stirred suspension of 3 (1.0 g, 47 mmol), water (40 mL), sodium thiosulfate (10.0 g, 63.3 mmol) and NaOH (3.5 g, 87.5 mmol) maintained at 60° C. The mixture was allowed to stir at 60° C. for 4 h, then cooled to room temperature, and extracted with CHCl₃. The organic layer was washed with water, dried over anhydrous MgSO₄ and concentrated under reduced pressure to give 1.5 g of the crude intermediate 4,9-dimethoxynaphtho[2,3-b]thiophene (4).

To 4 (1.5 g) in 1,2-dichloroethane (120 mL) were added acetyl chloride (4.3 mL, 55 mmol) and AlCl₃ (7.3 g, 55 mmol). The resulting mixture was stirred at 5±2° C. for 4 h and then poured into ice water and acidified with conc. HCl. The organic layer was washed with water, dried over anhydrous MgSO₄ and evaporated. CrO₃ (0.5 g, 50 mmol) and HOAc (12 mL) were added to the residue. The mixture was stirred at room temperature for 8 h, and then i-PrOH (30 mL) was added, and the resulting solution extracted with CHCl₃. The organic layer was washed with saturated NaHCO₃, dried over anhydrous MgSO₄ and evaporated. Column chromatography (silica gel, CHCl₃) gave compounds 5, 6, and 7 in 20, 11, and 9% yields, respectively.

Compound 5, yellow needles from CHCl₃-EtOH (mp 139–140° C.). Rf value=0.15, CHCl₃. IR (KBr) 1650, 1680

(C=O) cm$^{-1}$. $^1$H-NMR (CDCl$_3$) δ 2.68 (s, 3H, CH$_3$), 7.77 (dt, J=2.0, 7.2 Hz, 1H, H-6), 7.80 (dt, J=2.0, 7.2 Hz, 1H, H-7), 7.91 (s, 1H, H-3), 8.21(dd, J=2.0, 7.2 Hz, 1H, H-8), 8.22 (dd, J=2.0, 7.2 Hz, 1H, H-5). $^{13}$C-NMR (CDCl$_3$) δ 30.6 (CH$_3$), 126.9 (C-5), 127.7 (C-8), 132.8 (C-4a), 133.5 (C-8a), 133.9 (C-6), 134.3 (C-7), 134.8 (C-3), 139.1 (C-3a), 144.2 (C-2), 147.2 (C-9a), 178.1 (C-4), 179.0 (C-9), 197.3 (C-2-C=O). MS m/z (256, M$^+$). Anal. calcd for C$_{14}$H$_8$O$_3$S: C, 65.62; H, 3.15; Found: C, 65.53; H, 3.13%.

Compound 6 (mp 244–245° C.). Rf value=0.26, CHCl$_3$. IR (KBr) 1650, 1680 (C=O) cm$^{-1}$. $^1$H-NMR (CDCl$_3$) δ 2.70 (s, 3H, CH$_3$), 7.78 (dt, J=2.0, 7.2 Hz, 1H, H-6), 7.80 (dt, J=2.0, 7.2 Hz, 1H, H-7), 8.18 (s, 1H, H-2), 8.20 (dd, J=2.0, 7.2 Hz, 1H, H-8), 8.22 (dd, J=2.0, 7.2 Hz, 1H, H-5). $^{13}$C-NMR (CDCl$_3$) δ 26.9 (CH$_3$), 126.8 (C-5), 127.6 (C-8), 129.7 (C-2), 132.8 (C-4a), 133.4 (C-8a), 133.8 (C-6), 134.4 (C-7), 142.9 (C-3), 148.9 (C-3a), 150.1 (C-9a), 179.2 (C-9), 179.3 (C-4), 190.5 (C-3-C=O). MS m/z (256, M$^+$). Anal. calcd for C$_{14}$H$_8$O$_3$S: C, 65.62; H, 3.15. Found: C, 65.56; H, 3.11%.

Compound 7 (mp 146–147° C.). Rf value=0.35, CHCl$_3$. IR (KBr) 1650, 1680 (C=O) cm$^{-1}$. $^1$H-NMR (CDCl$_3$) δ 2.75 (s, 3H, CH$_3$), 7.70 (d, J=5.4 Hz, 1H, H-3), 7.80 (d, J=5.4 Hz, 1H, H-2), 8.33 (br.s, 2H, H-5, H-6), 8.74 (s, 1H, H-8). $^{13}$C-NMR (CDCl$_3$) δ 26.8 (CH$_3$), 126.7 (C-8), 126.8 (C-3), 127.7 (C-5), 132.7 (C-6), 133.7 (C-8a), 134.6 (C-2), 135.8 (C-3a), 140.5 (C-7), 142.7 (C-4a), 145.3 (C-9a), 177.1 (C-4), 178.3 (C-9), 196.4 (C-7-C=O). MS m/z (256, M$^+$). Anal. calcd for C$_{14}$H$_8$O$_3$S: C, 65.62; H, 3.15. Found: C, 65.49; H, 3.17%.

Example 15

2,7-Diacetyl-(9) and 3,7-Diacetyl naphtho[2,3-b]thiophene-4,9-dione (10)

To a mixture of 6 (2.0 g, 8 mmol) and 28% ammonia water (100 mL), CuSO$_4$ 0.05 g, 0.3 mmol) and Cu powder (5 g, 79 mmol) were added. This mixture was refluxed for 36 h, with 5 mL of 28% ammonia water added every 6 h during the heating. The reaction mixture was filtered while hot, and the filtrate was acidified with conc. HCl and cooled to form a precipitate. Two g of the precipitate were dissolved in a mixture of HOAc (22 mL) and acetic anhydride (14 mL). To the resulting solution, newly melted ZnO (0.3 g, 3.7 mmol) was added. Then the mixture was refluxed for 1.5 h, and an equal volume of H$_2$O was added to the hot mixture. This mixture was cooled and filtered to give a solid material, which was dried and dissolved in ClCH$_2$CH$_2$Cl to form reactant solution A.

To reactant solution B containing acetic anhydride (3 mL, 29.4 mmol), AlCl$_3$ (3.5 g, 26.2 mmol) and 1,2-dichloroethane (150 mL), the reactant solution A was added dropwise at 30–40° C. The mixture was stirred at the same temperature for 4 h. After the solvent was removed in vacuum, the residue was dissolved in CHCl$_3$ (100 mL) and HOAc (2 mL), and CrO$_3$ (0.24 g, 2.4 mmol) was added. The reaction was carried out at 30±2° C. for 3 h while stirring. Then the reaction mixture was neutralized with 5% NaHCO$_3$ and extracted with CHCl$_3$. The organic layer was washed with saturated NaCl, dried over anhydrous MgSO$_4$ and evaporated. The residue was purified by column chromatography on silica gel eluting with CHCl$_3$:MeOH (100:1) to obtain compounds 5 (9% yield), 9 (13% yield), and 10 (14% yield).

Compound 9 (mp 202–204° C.). Rf value=0.11, CHCl$_3$:MeOH=100:1. IR (KBr) 1650, 1680 (C=O) cm$^{-1}$. $^1$H NMR (CDCl$_3$) δ 2.68 (s, 3H, 2-COCH$_3$), 2.75 (s, 3H, 7-COCH$_3$), 7.96 (s, 1H, H-3), 8.33 (br.s, 2H, H-5, H-6), 8.70 (s, 1H, H-8). $^{13}$C NMR (CDCl$_3$) δ 26.0 (C-7-CH$_3$), 29.6 (C-2-CH$_3$), 126.5 (C-5), 126.6 (C-8), 131.9 (C-6), 134.5 (C-3, C-8a), 138.2 (C-3a), 140.3 (C-7, C-4a), 143.3 (C-2), 146.2 (C-9a), 176.4 (C-4), 177.3 (C-9), 195.4 (C-7-C=O), 195.9 (C-2-C=O). MS m/z (298, M$^+$). Anal. calcd for C$_{16}$H$_{10}$O$_4$S: C, 64.42; H, 3.36. Found: C, 64.38; H, 3.32%.

Compound 10 (mp 180–182° C.). Rf value=0.18, CHCl$_3$:MeOH=100:1. IR (KBr) 1650, 1680, 1700 (C=O) cm$^{-1}$. $^1$H NMR (CDCl$_3$) δ 2.70 (s, 3H, 3-COCH$_3$), 2.75 (s, 3H, 7-COCH$_3$), 8.19 (s, 1H, H-2), 8.33 (br.s, 2H, H-5, H-6), 8.74 (s, 1H, H-8). $^{13}$C NMR (CDCl$_3$) δ 26.9 (C-3-CH$_3$), 27.0 (C-7-CH$_3$), 127.4 (C-8), 127.8 (C-5), 129.7 (C-2), 133.0 (C-6), 133.6 (C-8a), 136.0 (C-4a), 141.2 (C-7), 142.9 (C-3), 149.4 (C-3a), 151.0 (C-9a), 177.5 (C-4), 178.5 (C-9), 190.5 (C-3-C=O), 196.4 (C-7-C=O). MS m/z (298, M$^+$). Anal. calcd for C$_{16}$H$_{10}$O$_4$S: C, 64.42; H, 3.36. Found: C, 64.45; H, 3.33%.

Example 16

Biological Activity

The unsubstituted (3), two mono-acetyl (5, 6), and two di-acetyl (9, 10) derivatives were tested for cytotoxicity in a preliminary KB cell assay. The parent compound 3 and the 3-acetyl derivative 6 showed similar potency in this assay with ED$_{50}$ values of 6.5 and 5 μM, respectively. The potency increased (ED$_{50}$~1.5 μM) when acetyl groups were added at the 2-(5) or the 2, 7-(9) positions. Compound 10 with 3,7-disubstitution was the most potent in this assay with an ED$_{50}$ value of 0.45 μM.

Compounds 5, 6, and 9 were also tested in NCI's in vitro human tumor cell line assay; the data from seven cancer types are shown in Table 3. All three compounds were active against all cell lines with similar mean log GI$_{50}$ values ranging from –5.67 to –6.15. (GI$_{50}$ is the molar concentration causing 50% cell growth inhibition; compounds with log GI$_{50}$ <–4 are considered active.) The activity order roughly paralleled that in the KB cell assay with compound 9 showing greater activity, especially against HCT-15 colon and MCF breast cancer cell lines. Compound 9 was quite active against leukemia cell lines with log GI$_{50}$ values of –7.61 against the SR and –7.18 against MOLT-4 cells; compound 6 also showed significant cytotoxicity in the latter cell line (ED$_{50}$ <–8).

In summary, acetyl derivatives of 4H, 9H-naphtho[2,3-b]thiophene-4,9-dione show promise as lead compounds for the further development of anticancer agents. Synthesis and cytotoxic evaluation of additional derivatives of this nucleus will be reported in a subsequent article.

TABLE 3

Inhibition of In Vitro Cancer Cell Lines by Compounds 5, 6, and 9

| Cell Line | Cytotoxicity log GI$_{50}$ (M)$^{a,b}$ | | |
|---|---|---|---|
| | 5 | 6 | 9 |
| Leukemia | | | |
| CCRF-CEM | –6.00 | –5.81 | –6.74 |
| MOLT-4 | –5.69 | <–8.00 | –7.18 |
| SR | — | — | –7.61 |
| Non-Small Cell Lung Cancer | | | |
| NCI-H23 | –6.35 | –5.98 | –6.22 |

TABLE 3-continued

Inhibition of In Vitro Cancer Cell Lines by Compounds 5, 6, and 9

| Cell Line | Cytotoxicity log GI$_{50}$ (M)$^{a,b}$ | | |
|---|---|---|---|
| | 5 | 6 | 9 |
| NCI-H460 | −6.34 | −5.88 | −6.44 |
| NCI-H552 | −6.39 | −5.76 | −6.65 |
| Colon Cancer | | | |
| HCT-15 | −6.15 | −4.76 | −7.39 |
| SW-620 | −6.34 | −5.66 | −6.69 |
| CNS Cancer | | | |
| SF-539 | −6.12 | −5.69 | −6.45 |
| SNB-19 | −6.30 | −5.75 | −5.87 |
| Melanoma | | | |
| LOX IMVI | −6.46 | −5.63 | −6.66 |
| SK-MEL-5 | −6.46 | −6.77 | −6.76 |
| Ovarian Cancer | | | |
| IGROV1 | −5.75 | −5.61 | −6.37 |
| OVCAR-3 | −6.30 | −5.45 | −6.48 |
| Breast Cancer | | | |
| MCF 7 | −5.77 | −5.68 | −6.50 |
| MCF 7/ADR-RES | −5.72 | −5.54 | −6.49 |
| MDA-MB-435 | −6.47 | −6.49 | −6.75 |
| MDA-N | −5.92 | −6.03 | −6.50 |
| Mean Value$^c$ | −5.71 | −5.67 | −6.15 |

$^a$Data obtained from NCI's in vitro disease-oriented tumor cells screen.
$^b$Data are an average of at least two testings.
$^c$Mean value over all cell lines tested.

The foregoing is illustrative of the present invention, and is not to be construed as limiting thereof. The invention is defined by the following claims, with equivalents of the claims to be included therein.

We claim:

1. A method for inhibiting cellular mitosis in a tumor cell, said method comprising contacting a tumor cell with a compound in an amount effective to inhibit cellular mitosis therein, said compound selected from the group consisting of compounds of Formula I and compounds of Formula II:

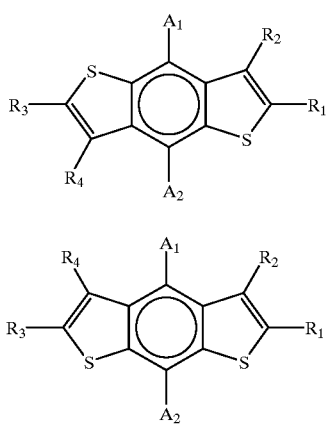

wherein:
$R_1$, $R_2$, $R_3$ and $R_4$ are each independently selected from the group consisting of:
hydrogen alkyl carboxy, alkoxy, hydroxyalkyl, alkylcarbonyl; alkylcarbonyloxy; alkyl substituted with alkylcarbonyloxy, thiophenylcarbonyl; nitro and cyano;
thiophenyl and thiophenylthiophenyl, each of which may be unsubstituted or substituted with alkyl, carboxy, alkoxy, hydroxyalkyl, alkylcarbonyl; alkylcarbonyloxy; alkyl substituted with alkylcarbonyloxy, nitro or cyano;
subject to the proviso that at least one of $R_1$, $R_2$, $R_3$ and $R_4$ is not hydrogen;
$A_1$ and $A_2$ are each selected from the group consisting of =O, alkyl, alkoxy, and alkylcarbonyloxy;
and the pharmaceutically acceptable salts thereof.

2. A method according to claim 1, wherein three of $R_1$, $R_2$, $R_3$ and $R_4$ are hydrogen.

3. A method according to claim 1, wherein said compound is selected from the group consisting of compounds of Formula Ia and compounds of Formula IIa:

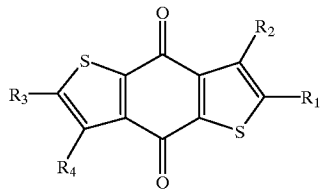

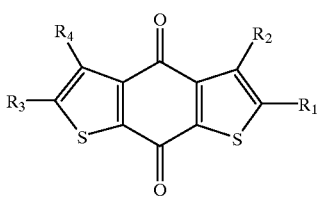

wherein:
$R_1$, $R_2$, $R_3$ and $R_4$ are each independently selected from the group consisting of:
hydrogen, alkyl, carboxy, alkoxy, hydroxyalkyl alkylcarbonyl, alkylcarbonyloxy, alkyl substituted with alkylcarbonyloxy thiophenylcarbonyl; nitro and cyano;
thiophenyl and thiophenylthiophenyl, each of which may be unsubstituted or substituted with alkyl, carboxy, alkoxy, hydroxyalkyl, alkylcarbonyl, alkylcarbonyloxy, alkyl substituted with alkylcarbonyloxy, nitro or cyano;
subject to the proviso that at least one of $R_1$, $R_2$, $R_3$ and $R_4$ is not hydrogen;
and the pharmaceutically acceptable salts thereof.

4. A method according to claim 1, wherein said compound is selected from the group consisting of compounds of Formula Ib and compounds of Formula IIb:

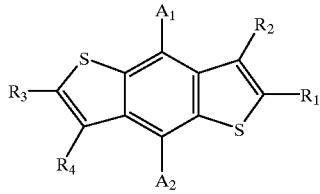

-continued

IIb

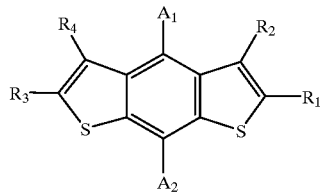

wherein:
R₁, R₂, R₃ and R₄ are each independently selected from the group consisting of:
hydrogen, alkyl carboxy, alkoxy, hydroxyalkyl, alkylcarbonyl, alkylcarbonyloxy; alkyl substituted with alkylcarbonyloxy, thiophenylcarbonyl, nitro and cyano;
thiophenyl and thiophenylthiophenyl, each of which may be unsubstituted or substituted with alkyl, carboxy, alkoxy, hydroxyalkyl, alkylcarbonyl, alkylcarbonyloxy, alkyl substituted with alkylcarbonyloxy, nitro or cyano;
subject to the proviso that at least one of $R_1$, $R_2$, $R_3$ and $R_4$ is not hydrogen;
$A_1$ and $A_2$ are each selected from the group consisting of alkyl, alkoxy, and alkylcarbonyloxy;
and the pharmaceutically acceptable salts thereof.

5. A method according to claim 1, said compound selected from the group consisting of:
2-Acetyl-4,8-dihydrobenzo[1,2-b:4,5-b']dithiophene-4,8-dione;
2-(1'-Hydroxyethyl)-4,8-dihydrobenzo[1,2-b:4,5-b']dithiophene-4,8-dione;
2-(1'-Acetoxyethyl)-4,8-dihydrobenzo[1,2-b:4,5-b']dithiophene-4,8-dione;
2,7-Diacetyl-4,8-dihydrobenzo[1,2-b:4,5-b']dithiophene-4,8-dione;
2,7-Bis(1'-hydroxyethyl)-4,8-dihydrobenzo[1,2-b:4,5-b']dithiophene-4,8-dione;
2,7-Bis(1'-acetoxyethyl)-4,8-dihydrobenzo[1,2-b:4,5-b']dithiophene-4,8-dione;
2-Acetyl-4,8-dihydrobenzo[1,2-b:5,4-b']dithiophene-4,8-dione;
2-(1'-Hydroxyethyl)-4,8-dihydrobenzo[1,2-b:5,4-b']dithiophene-4,8-dione;
2-(1'-Acetoxyethyl)-4,8-dihydrobenzo[1,2-b:5,4-b']dithiophene-4,8-dione;
2,7-Diacetyl-4,8-dihydrobenzo[1,2-b:5,4-b']dithiophene-4,8-dione;
2,7-Bis(1'-hydroxyethyl)-4,8-dihydrobenzo[1,2-b:5,4-b']dithiophene-4,8-dione;
2,7-Bis(1'-acetoxyethyl)-4,8-dihydrobenzo[1,2-b:5,4-b']dithiophene-4,8-dione;
and the pharmaceutically acceptable salts thereof.

6. A method for inhibiting cellular mitosis, said method comprising contacting a cell with a compound according to claim 1 in an amount effective to inhibit cellular mitosis.

7. A compound according to Formula III:

III

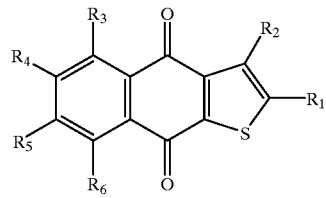

wherein:
$R_1$ and $R_2$ are each independently selected from the group consisting of:
carboxy, alkoxy, hydroxyalkyl, alkylcarbonyl, alkylcarbonyloxy, alkyl substituted with alkylcarbonyloxy, thiophenylcarbonyl; and nitro;
thiophenyl and thiophenylthiophenyl, each of which may be unsubstituted or substituted with alkyl, carboxy, alkoxy, hydroxyalkyl, alkylcarbonyl, alkylcarbonyloxy, alkyl substituted with alkylcarbonyloxy, nitro or cyano;
$R_3$, $R_4$, $R_5$ and $R_6$ are each independently selected from the group consisting of:
hydrogen, alkyl, carboxy, alkoxy, hydroxyalkyl, alkylcarbonyl, alkylcarbonyloxy, alkyl substituted with alkylcarbonyloxy, thiophenylcarbonyl; nitro and cyano;
thiophenyl and thiophenylthiophenyl, each of which may be unsubstituted or substituted with alkyl carboxy, alkoxy, hydroxyalkyl, alkylcarbonyl, alkylcarbonyloxy, alkyl substituted with alkylcarbonyloxy, nitro or cyano; subject to the proviso that at least one of $R_1$, $R_2$, $R_3$ and $R_4$ is not hydrogen;
and the pharmaceutically acceptable salts thereof.

* * * * *